(12) United States Patent
Wiita et al.

(10) Patent No.: US 8,636,724 B2
(45) Date of Patent: Jan. 28, 2014

(54) BALLOON ENCAPSULATED CATHETER TIP

(75) Inventors: Gregory D. Wiita, Jupiter, FL (US); Bruce E. Wiita, Jupiter, FL (US)

(73) Assignee: Poiesis Medical, LLC, Jupiter, FL (US)

( * ) Notice: Subject to any disclaimer, the term of this patent is extended or adjusted under 35 U.S.C. 154(b) by 183 days.

(21) Appl. No.: 12/912,349

(22) Filed: Oct. 26, 2010

(65) Prior Publication Data

US 2011/0098683 A1    Apr. 28, 2011

Related U.S. Application Data

(60) Provisional application No. 61/254,950, filed on Oct. 26, 2009.

(51) Int. Cl.
*A61M 25/00* (2006.01)
*A61M 25/10* (2013.01)

(52) U.S. Cl.
USPC ........ 604/544; 604/540; 604/509; 604/96.01; 604/101.01; 604/101.03; 604/101.05; 604/103; 604/103.06; 604/103.07

(58) Field of Classification Search
USPC ........ 604/540, 544, 509, 95.03, 96.01, 97.01, 604/101.01, 101.03, 101.05, 102.01, 604/102.02, 102.03, 103, 103.06
See application file for complete search history.

(56) References Cited

U.S. PATENT DOCUMENTS

| | | |
|---|---|---|
| 1,922,084 A | 8/1933 | Gerow |
| 2,649,092 A | 8/1953 | Wallace |
| 2,854,983 A | 10/1958 | Baskin |
| 2,919,697 A | 1/1960 | Kim |
| 3,045,677 A | 7/1962 | Wallace |
| 3,190,291 A | 6/1965 | Foley |
| 3,344,791 A | 10/1967 | Foderick |
| 3,438,375 A | 4/1969 | Ericson |
| 3,592,197 A | 7/1971 | Cohen |
| 3,811,448 A | 5/1974 | Morton |
| 3,915,171 A | 10/1975 | Shermeta |
| 3,938,530 A | 2/1976 | Santomieri |
| 3,954,110 A | 5/1976 | Hutchison |
| 3,982,544 A | 9/1976 | Dyck |
| 4,022,216 A | 5/1977 | Stevens |
| 4,154,243 A | 5/1979 | Patel et al. |
| 4,157,094 A | 6/1979 | Patel |
| 4,211,233 A | 7/1980 | Lin |
| 4,219,026 A | 8/1980 | Layton |
| 4,222,384 A | 9/1980 | Birtwell |
| 4,224,929 A | 9/1980 | Furihata |
| 4,233,983 A | 11/1980 | Rocco |
| 4,342,316 A | 8/1982 | Rosenberg |
| 4,351,342 A | 9/1982 | Wiita et al. |
| 4,496,345 A * | 1/1985 | Hasson ............... 604/103 |

(Continued)

FOREIGN PATENT DOCUMENTS

| | | |
|---|---|---|
| WO | 2011056587 | 5/2011 |
| WO | 2011056588 | 5/2011 |

*Primary Examiner* — Adam Marcetich
(74) *Attorney, Agent, or Firm* — McHale & Slavin, P.A.

(57) ABSTRACT

This invention is generally related to catheters for insertion into a body cavity, duct or vessel, and more particularly to a tip or plug for a catheter. The catheter tip is constructed and arranged to form a seal on the end portion of the catheter tube, while a sleeve secured or formed integrally to the tip cooperates with the catheter tube to form a first balloon that encapsulates the tip of the catheter and a second balloon that positions the catheter within the body cavity, duct or vessel.

32 Claims, 14 Drawing Sheets

(56) References Cited

U.S. PATENT DOCUMENTS

| | | | | |
|---|---|---|---|---|
| 4,555,242 A | * | 11/1985 | Saudagar | 604/103.08 |
| 4,575,371 A | | 3/1986 | Nordqvist et al. | |
| 4,861,337 A | * | 8/1989 | George | 604/103.09 |
| 5,042,976 A | * | 8/1991 | Ishitsu et al. | 604/96.01 |
| 5,250,029 A | | 10/1993 | Lin et al. | |
| 5,599,321 A | | 2/1997 | Conway et al. | |
| 5,662,609 A | * | 9/1997 | Slepian | 604/101.03 |
| 5,707,357 A | | 1/1998 | Mikhail et al. | |
| 5,718,712 A | | 2/1998 | Bonnal et al. | |
| 6,283,940 B1 | | 9/2001 | Mulholland | |
| 6,443,941 B1 | * | 9/2002 | Slepian et al. | 604/522 |
| 6,506,179 B1 | | 1/2003 | Tiefenthal et al. | |
| 2002/0077594 A1 | * | 6/2002 | Chien et al. | 604/103.02 |
| 2002/0099332 A1 | * | 7/2002 | Slepian et al. | 604/96.01 |
| 2003/0229332 A1 | * | 12/2003 | Intoccia | 604/508 |
| 2004/0106900 A1 | * | 6/2004 | Triebes et al. | 604/104 |
| 2005/0085770 A1 | * | 4/2005 | Don Michael | 604/101.03 |
| 2006/0025753 A1 | * | 2/2006 | Kubalak et al. | 604/544 |
| 2006/0129093 A1 | * | 6/2006 | Jackson | 604/96.01 |
| 2007/0203445 A1 | * | 8/2007 | Kaye et al. | 604/6.16 |
| 2009/0221992 A1 | | 9/2009 | Hannon et al. | |
| 2010/0222811 A1 | * | 9/2010 | Gellman | 606/228 |
| 2011/0060317 A1 | * | 3/2011 | Frojd | 604/544 |
| 2011/0094655 A1 | | 4/2011 | Wiita et al. | |

* cited by examiner

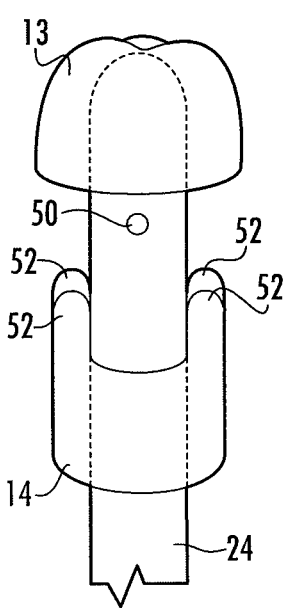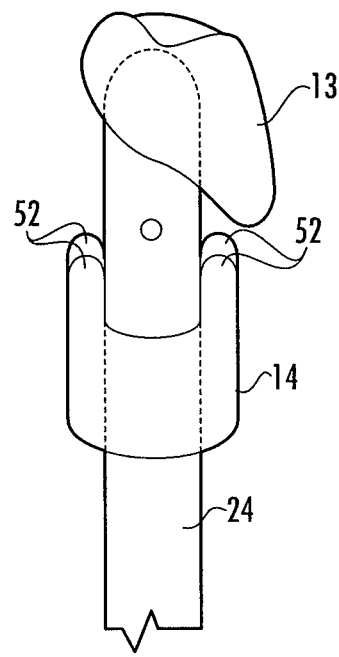
FIG. 19　　　　　　　　FIG. 20
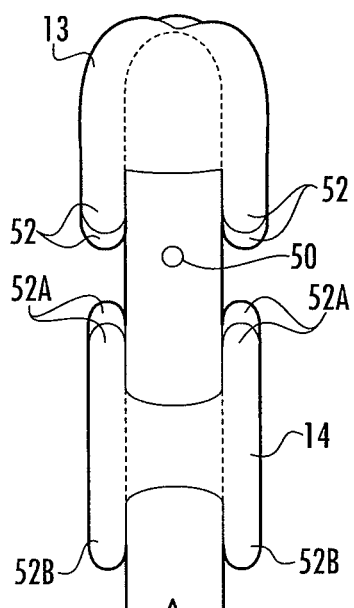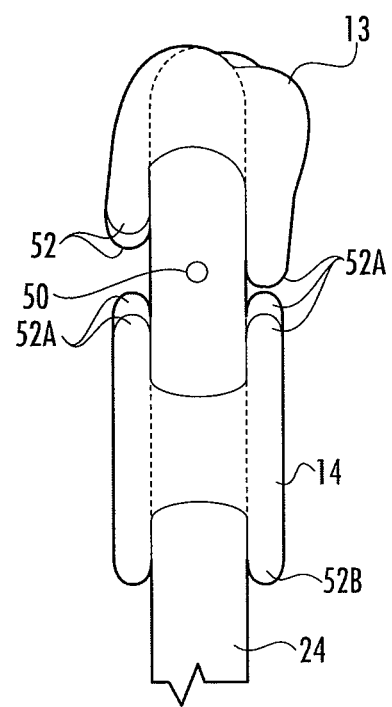
FIG. 21　　　　　　　　FIG. 22

BALLOON ENCAPSULATED CATHETER TIP

CROSS REFERENCE TO RELATED APPLICATIONS

This application claims benefit of the filing date of Provisional Application 61/254,950, filed on Oct. 26, 2009, the contents of which are herein incorporated by reference. This application is also related to U.S. Pat. No. 4,351,342 entitled, "BALLOON CATHETER", filed on Sep. 28, 1982, and issued to Bruce E. Wiita and J. Michael Teets, the contents of which are herein incorporated by reference.

FIELD OF THE INVENTION

This invention relates to medical devices, and more specifically to a balloon encapsulated catheter tip or plug that is constructed and arranged for insertion into a body cavity, duct or vessel.

BACKGROUND OF THE INVENTION

This invention is generally related to catheters for insertion into a body cavity, duct or vessel, and more particularly to a tip or plug for a catheter. The catheter tip is constructed and arranged to form a seal on the end portion of the catheter tube, while a sleeve secured or formed integrally to the tip cooperates with the catheter tube to form a first balloon that encapsulates the tip of the catheter and a second balloon that positions the catheter within the body cavity, duct or vessel. For a better understanding of this invention, it will be described in connection with a urinary catheter, which is one area where this invention has commercial potential.

Urinary Catheters have been used for many years. A particularly well known urinary catheter is the Foley catheter. The Foley catheter includes a flexible tube made of latex and/or silicone material and has two internal lumens extending substantially parallel along the length of the tube. A balloon is positioned near the distal end of the tube for holding the catheter in position within the bladder of a patient. The catheter is positioned within the patient and fluid is introduced through one of the lumens to inflate the balloon to retain the catheter in the desired position. A drainage port or eye is located at the distal end of the catheter to allow the urine to pass through one of the lumens of the catheter tube for urine drainage purposes. However, the Foley catheter, like all other currently and commercially available catheters, suffers from the same or a similar drawback in that they have a tip that extends beyond the balloon. This tip often bears or scrapes against the liner of the bladder causing trauma to the bladder lining and is associated with numerous medical problems. A further problem relates to the position of the drain port(s) causing patient discomfort when the mucosal lining is drawn into the drain port(s). Some examples of the medical problems associated with the current catheter devices include discomfort, spasms and bleeding, as well as more serious drawbacks such as bacteria in the blood stream, e.g. Urosepsis and urinary tract infections.

Therefore what is needed in the art is a catheter tip that includes a first balloon positioned to encapsulate the tip of the catheter and a second balloon to position the catheter within the urinary tract. The first balloon should be constructed and arranged to cushion the catheter tip from traumatizing and irritating the internal wall of the cavity, duct or vessel. Moreover, the balloon should be connected to the tip so as to prevent the tip from moving relative to the balloon.

PRIOR ART

Numerous types of catheters are known in the prior art. For example, U.S. Pat. No. 4,022,216 discloses a urological catheter having at its distal portion a pair of balloons which are inflatable from the proximal end of the catheter. In the inflated position, the one of the balloons completely covers the distal tip of the catheter to serve as a cushion for preventing damage to the patient's bladder, while the other balloon serves to anchor the catheter in sealing relation to the discharge passage of the bladder. A drainage opening in the catheter wall is disposed intermediate the balloons. While the '216 patent discloses dual balloons, the balloon which encloses the distal end is connected to the catheter along the side of the catheter body. This connection allows the tip to move relative to the balloon and can easily cause top over and blockage of the drainage aperture.

U.S. Pat. No. 4,342,316 discloses a catheter comprising an elongated shaft having an inflation lumen extending along the shaft, and a drainage lumen extending through the shaft. The catheter has a proximal end, a distal end, and a distal end portion. The catheter also has an elastic sleeve on the distal end portion of the catheter and opposed ends. The sleeve is bonded to the distal end portion in spaced circumferential zones adjacent the opposed ends of the sleeve and along longitudinal lines at least a substantial distance between the zones on opposed sides of the distal end portion. The catheter has an inflation opening beneath the sleeve communicating with the inflation lumen, and at least one drainage eye proximal the sleeve and communicating with the drainage lumen. One of the major disadvantages of the '316 patent is that the tip of the catheter is exposed and can damage any tissue structure that the catheter may be inserted within.

U.S. Pat. No. 4,575,371 discloses a urinary catheter with a retention member in the form of an expandable balloon. The expandable balloon is arranged below the inlet opening and so designed that in its inflated condition a portion projects forward past the catheter tip at some distance from the inlet opening. A shortcoming of the '371 patent, however, includes the fact that the drainage aperture is placed at the distal end of the catheter, resulting in a greater tendency to have the mucosal lining of the bladder being drawn into the drainage port when in use. Moreover, only a single balloon is connected to the body of the catheter and is connected in such a manner that the tip of the catheter can move relative to the balloon.

U.S. Publication 2009/0221992 discloses a fluid drainage catheter. The catheter comprises a catheter tube having proximal and distal ends and a cylindrical wall with a lumen extending generally from the proximal to the distal end to permit the passage of fluid therethrough. The catheter tube is formed such that the proximal end has a closed tip for insertion of the catheter tube into a body cavity, and the distal end has an opening for the drainage of fluid from the body cavity through the catheter tube. The cylindrical wall has an outer surface with at least one defined external flow path extending generally in a longitudinal direction from a point in proximity to the closed tip to a point distally thereof. A drainage eye is associated with the defined external flow path and extends completely through the catheter tube from the outer surface to the lumen to permit fluid in the flow path to pass through the drainage eye into the lumen. A drawback to the '992 catheter is that the tip is not completely covered increasing the risk of contact with tissue structures, resulting in damage and leading to increased risk of infection.

SUMMARY OF THE INVENTION

The needs, disadvantages and limitations of the background art discussed above are overcome by the present invention. The instant invention is generally related to catheters, and more specifically, the instant invention provides a catheter assembly or catheter tip that includes a first balloon constructed and arranged to encapsulate the tip of the catheter to prevent the drawbacks of the prior art, and a second balloon to position the catheter within a body duct, cavity, or vessel. The catheter tip includes a cap having a stem portion and a sleeve portion secured to or integrally formed with the cap. The tip and sleeve are preferably constructed of resiliently flexible biocompatible material(s). The cap portion of the tip is constructed and arranged to be attached to the distal end of a catheter tube while the optional stem is inserted into the drain lumen of the catheter tube. The attached sleeve portion is extended over the outer surface of the end portion of the catheter tube and is selectively attached to the outer surface of the catheter tube in a manner that forms a first balloon positioned to encircle the cap at the distal end of the tube, and at least one second balloon positioned along the catheter tube to retain and/or position the catheter within a body cavity, duct or vessel. The balloons are expandable by admitting a preferably sterile fluid through one or more control lumen(s) extending through the catheter tube. The control lumens extend along the catheter tube substantially parallel to the drain lumen. Each control lumen is preferably provided with at least one aperture extending through the side wall of the catheter tube positioned in the area of one or more of the balloons to allow the fluid to enter the balloon from the lumen. The tip and sleeve are both preferably made of a biocompatible elastomeric material such as, but not limited to, natural rubber latex, synthetic rubber, plastic and silicone and may be prepared, as is known in the art, to include additives, suspensions and/or coatings specially utilized in the process of fabricating catheter balloons or used to prevent sticking together in storage or enhance lubricity. In addition, the inner and/or outer surfaces of the sleeve may include thick and/or thin sections, ribs or portions to cause the balloon to inflate to a desired shape. The tip and sleeve may be fabricated by any suitable process which may include but should not be limited to injection molding, dipping, vacuum forming, roto-molding, blow molding or suitable combination(s) thereof. In a most preferred embodiment, the sleeve is formed in an inside-out arrangement. After forming, the sleeve portion is preferably rolled, much like that of a condom. The tip is assembled to the catheter tube by inserting the stem portion of the plug into the central lumen of the catheter tube until the lower surface of the cap contacts the distal end of the catheter tube. Adhesive, solvents, fillers, radio frequency (RF) welding, laser welding or suitable combinations thereof may be utilized to secure the tip to the tube and/or seal the distal end of the catheter tube. The sleeve material may then be rolled over the outer surface of the catheter tube. At least two spaced apart and circumferentially extending bands of adhesive are positioned about the end portion of the catheter tube to secure the sleeve to the outer surface of the tube while forming the two balloons. Varying the width of the adhesive bands or distance between the adhesive bands allows the size of the balloons to be varied. It should be noted that solvents, radio frequency (RF) welding, laser welding or suitable combinations thereof may be utilized to secure the sleeve to the outer surface of the tube forming the two balloons. It should also be noted that the sleeve portion may be dipped into a solution that serves to expand the sleeve material before or after attachment to the catheter tube, such as an alcohol-based fluid, benzene, ether or the like. This expansion may allow for the sleeve to be easily rolled over the outer surface of the catheter tube, or alternatively, slid over the catheter tube, if left un-rolled. It should further be noted that the portion of the sleeve between the bands of adhesive may be removed, or the second balloon may be formed from a second sleeve of material without departing from the scope of the invention.

When assembled, the balloons may be expanded by admitting a fluid through one or more of the control lumens which open into the area of one or both of the balloons so that the sleeve material is expanded in a radial and/or axial direction so that the distal balloon extends beyond the distal surface of the tip, and as a result, serves as a barrier between the tip and the lining of the bladder.

Thus, it is an object of this invention to provide a unique construction for a catheter tip.

It is another object of this invention to provide a tip for a catheter wherein the tip is constructed and arranged to form a balloon to prevent the distal end of the catheter from impinging against the inner wall of a body duct, cavity or vessel.

It is yet another object of this invention to provide a tip for a catheter that includes an elongated sleeve secured thereto which cooperates with the side wall of the catheter tube for forming at least one balloon along the end portion of the catheter.

It is yet another object of this invention to provide a duct, cavity or vessel catheter that includes a protective balloon on the distal end of the catheter.

It is still yet another object of this invention to provide a catheter that includes a first balloon to circumscribe the tip of the catheter and a second balloon to position the catheter within a body duct, cavity or vessel.

Still another object of this invention is to provide a urinary catheter having a first balloon to circumscribe the tip of the catheter and a second balloon to position the catheter within the urinary tract.

Still yet another object of this invention is provide a catheter or tip for a catheter having a balloon that, when inflated, extends radially and axially beyond the distal end of the catheter.

Yet a further object of the invention is to provide a catheter balloon that includes ribs or a combination of areas of different thicknesses to provide a shape or direct the expansion of the balloon in a desired direction or area.

Still another object of the invention is to provide a catheter balloon that includes lobes or a combination of areas of different thicknesses to provide a shape or direct the expansion of the balloon in a desired direction or area.

Still yet a further object of the invention is to provide a catheter balloon that includes a drain port positioned between two balloons to reduce or eliminate the tendency of the mucosal lining from being drawn into the drain port during use.

The foregoing and other features of the present invention will become more apparent from the following description and accompanying drawings.

BRIEF DESCRIPTION OF THE DRAWINGS

FIG. 19 is a perspective view of one embodiment of the instant invention illustrating at least one balloon having one or more lobes;

FIG. 20 is a perspective view of the embodiment of the instant invention shown in FIG. 19, illustrating one of the balloons in a misaligned position;

FIG. 21 is a perspective view of an alternative embodiment of the instant invention illustrating both balloons having one or more lobes at the distal ends, proximal beds, or combinations thereof;

FIG. 22 is a perspective view of the alternative embodiment of the instant invention shown in FIG. 21, illustrating one of the balloons in a misaligned position;

DETAILED DESCRIPTION OF THE INVENTION

Figure 1A:
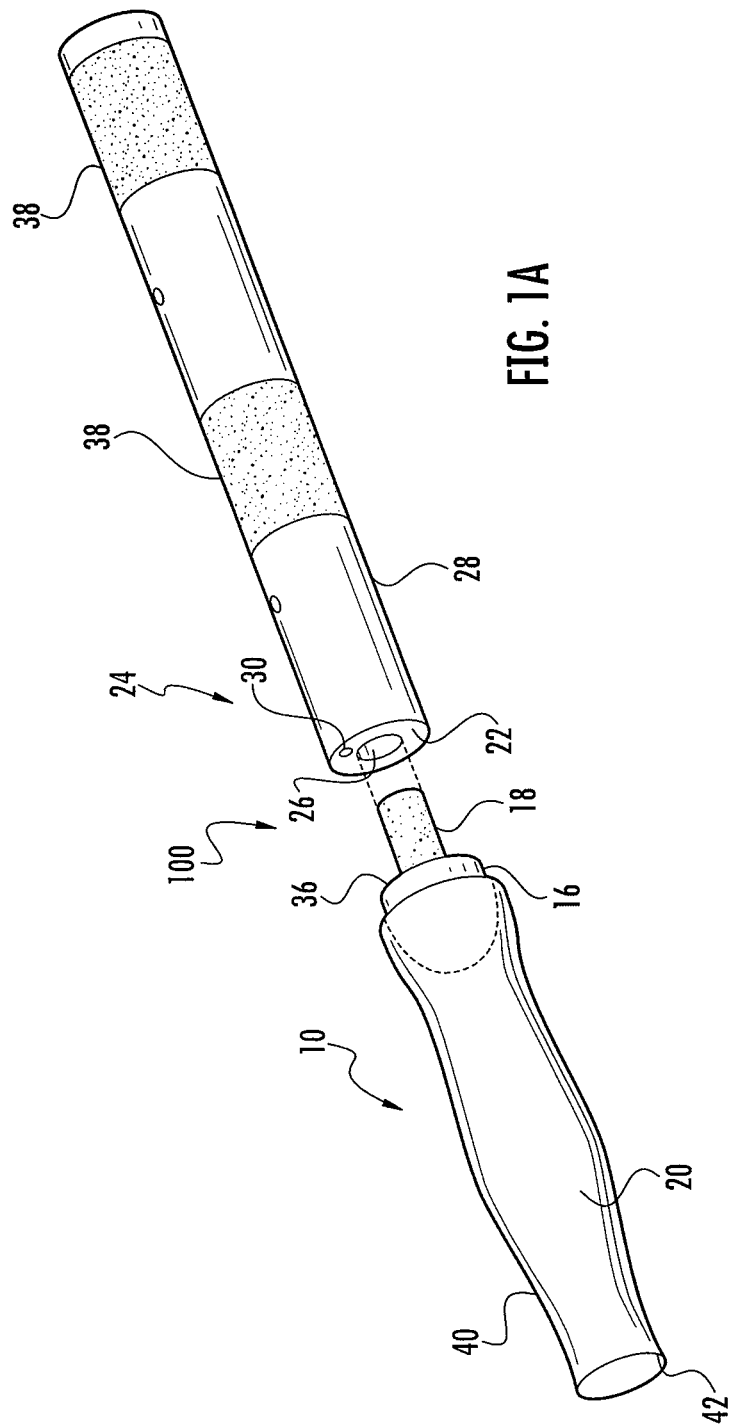
FIG. 1A is an exploded view of the catheter system in accordance with the instant invention, illustrating the tip and sleeve as well as a portion of the catheter tube.

While this invention is being described in its preferred embodiment as having a definitive catheter, it should be understood that the catheter is a commercially available item and that the invention is applied thereto and, as will be appreciated by one skilled in this technology, that the invention has utility for other types of catheters, some of which are disclosed in U.S. Pat. No. 4,351,342, supra.

Referring to FIGS. 1-6, the instant invention provides a catheter assembly 100 or catheter tip 10 that includes a first balloon 13 constructed and arranged to encapsulate the distal end 12 of the catheter to prevent the drawbacks of the prior art, and a second balloon 14 to position the catheter within a body duct, cavity, or vessel (not shown). The catheter tip 10 includes a cap 16 preferably having a stem portion 18 and a sleeve portion 20 secured to or integrally formed with the cap. The tip 10 and sleeve 20 are preferably constructed of resiliently flexible biocompatible material(s). The cap portion 16 of the tip 10 is constructed and arranged to be attached to the distal end 12 of a catheter tube 24 while the optional stem 18 is inserted into the drain lumen 26 of the catheter tube 24. The attached sleeve portion 20 is extended over the outer surface 28 of the end portion of the catheter tube 24 and is selectively attached to the outer surface 28 of the catheter tube 24 in a manner that forms a first balloon 13 positioned to encircle and extend beyond the cap 16 at the distal end of the tube, and at least one second balloon 14 positioned along the catheter tube 24 to retain and/or position the catheter 100 within a body cavity, duct or vessel.

Figure 1B:
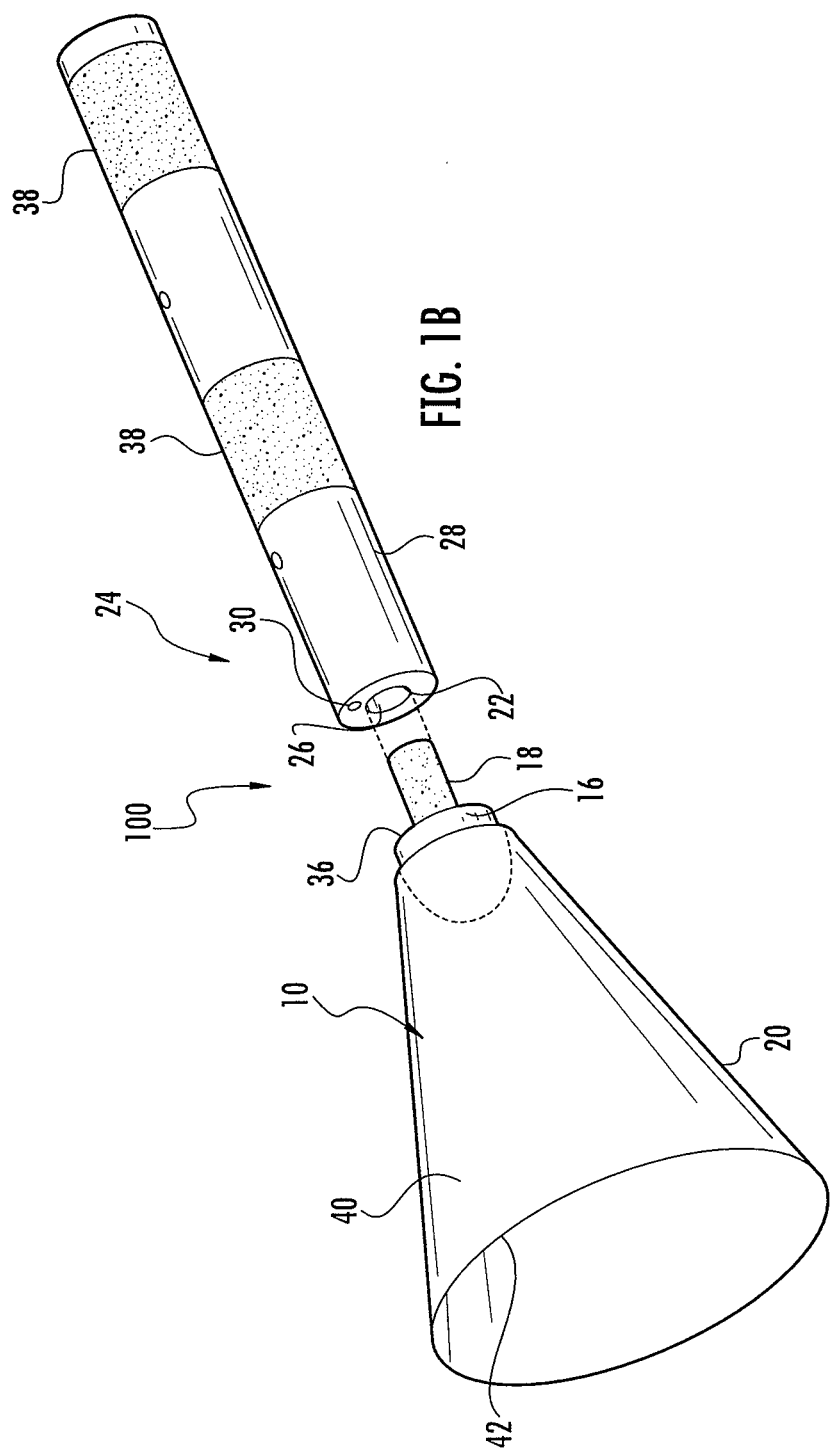
FIG. 1B is an exploded view of the catheter system in accordance with the instant invention, illustrating the tip and an alternative embodiment of the sleeve as well as a portion of the catheter tube.
Figure 2A:
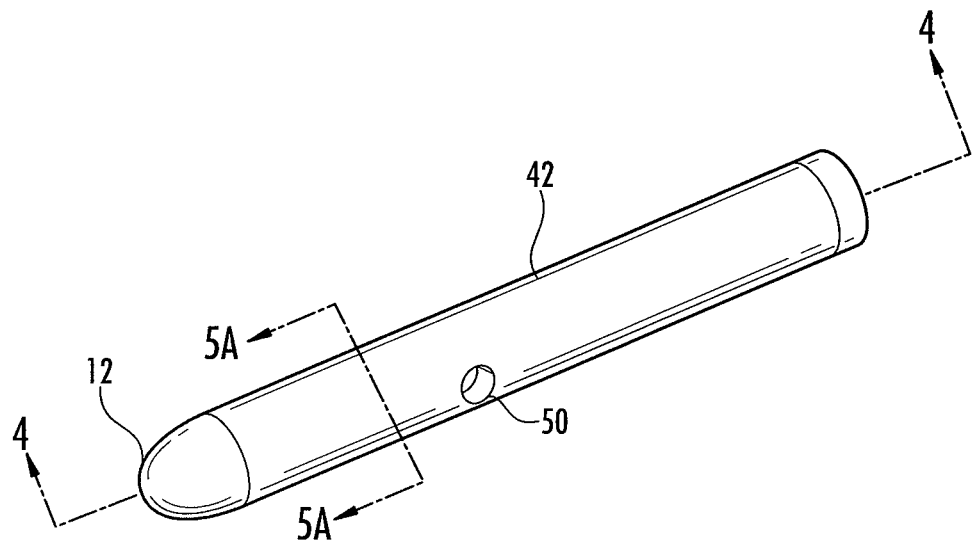
FIG. 2A is a perspective view of one embodiment of the catheter system in accordance with the instant invention.
Figure 2B:
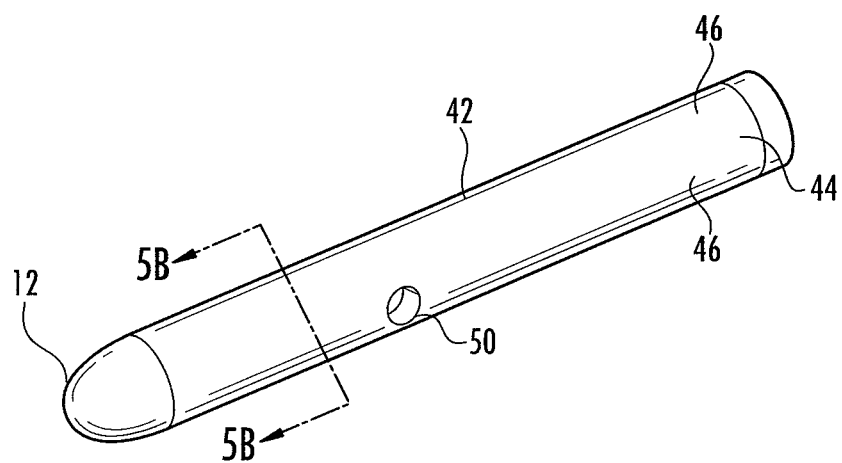
FIG. 2B is a perspective view of one embodiment of the catheter system in accordance with the instant invention, illustrating the regions of the catheter body which may contain varying thicknesses.
Figure 3:
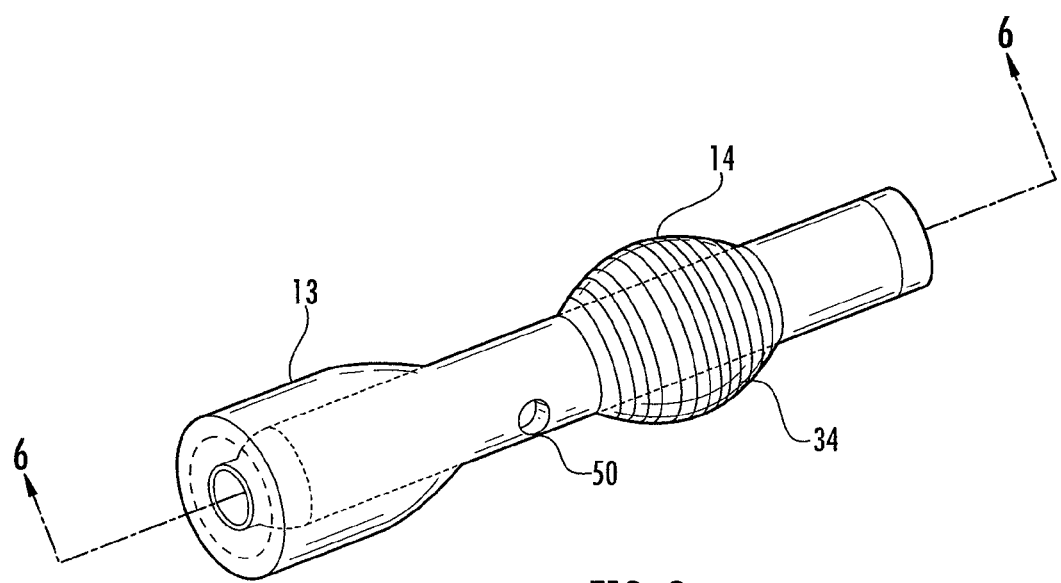
FIG. 3 is a perspective view of one embodiment of the instant invention illustrating the balloons in an expanded condition.
Figure 4:
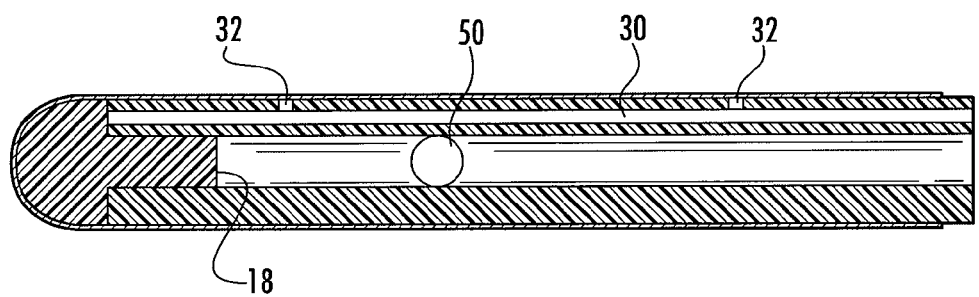
FIG. 4 is a section view taken along lines 4-4 of FIG. 2A illustrating the tip and sleeve assembled to the catheter tube as well as the lumens for passing urine and fluid.
Figure 5A:
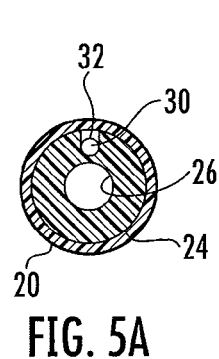
FIG. 5A is a section view taken along lines 5A-5A of FIG. 2A.
Figure 5B:
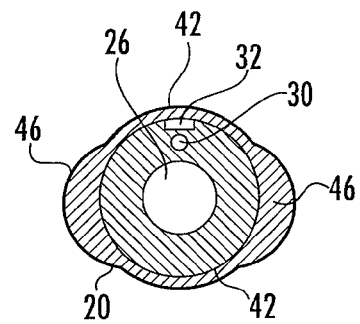
FIG. 5B is a section view taken along lines 5B-5B of FIG. 2B.
Figure 6:
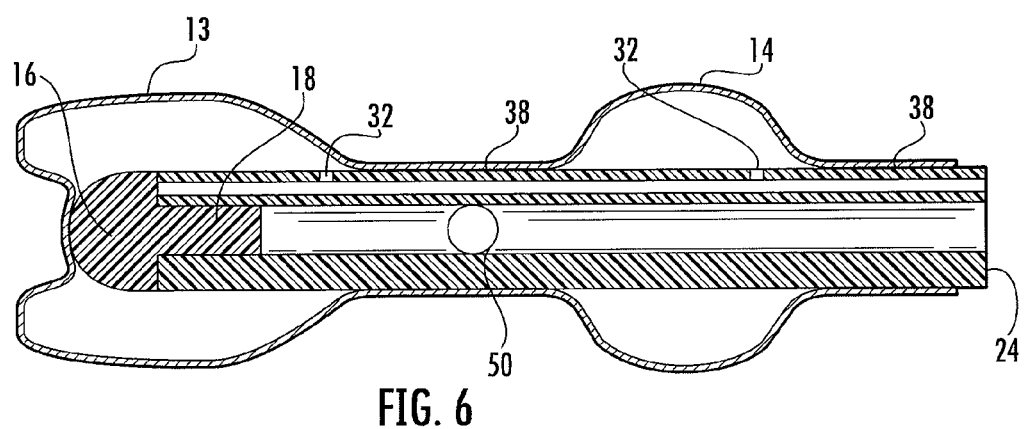
FIG. 6 is a section view taken along lines 6-6 of FIG. 3 illustrating the balloons in an expanded condition.
Figure 10:
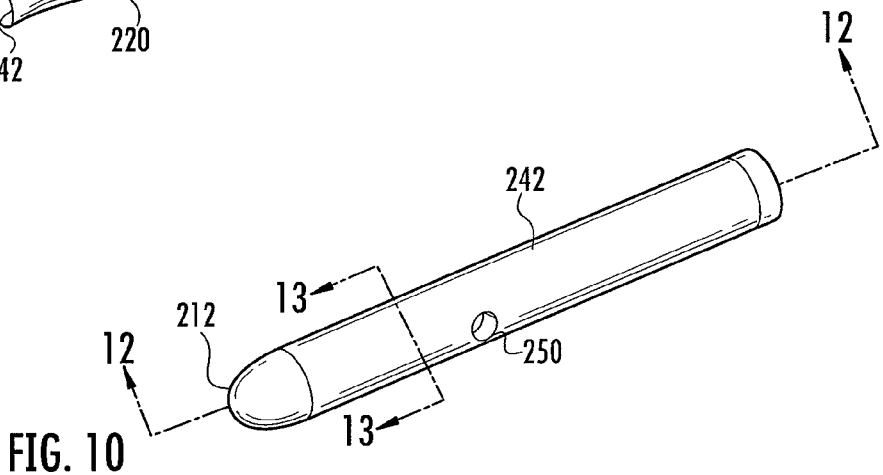
FIG. 10 is a perspective view of an alternative embodiment of the catheter system in accordance with the instant invention.
Figure 11:
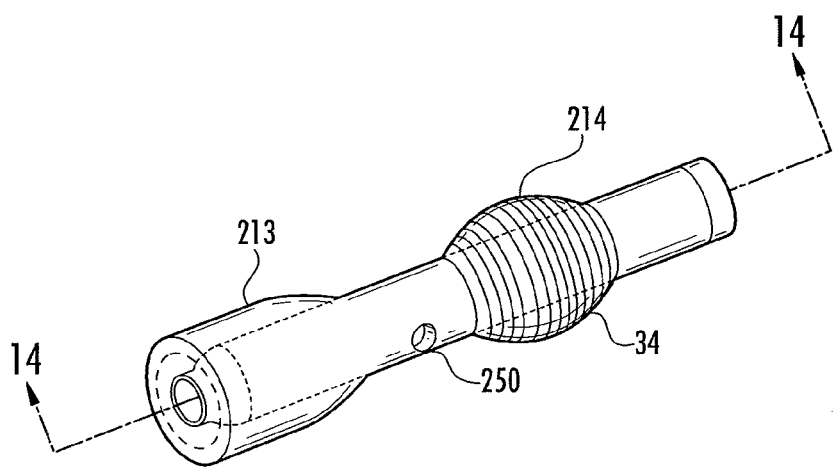
FIG. 11 is a perspective view of an alternative embodiment of the instant invention illustrating the balloons in an expanded condition.
Figure 12:
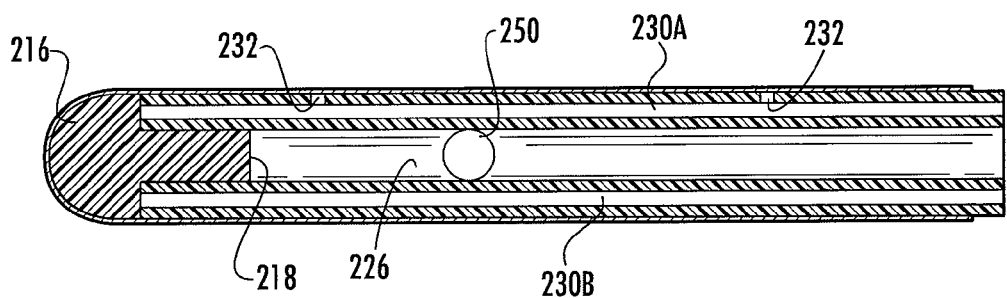
FIG. 12 is a section view taken along lines 12-12 of FIG. 10 illustrating the tip and sleeve assembled to the catheter tube as well as the lumens for passing urine and fluid.
Figure 13:
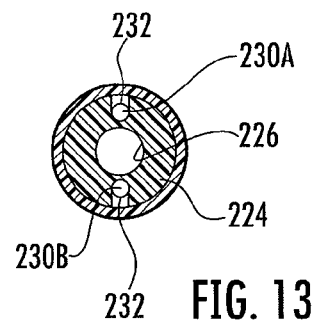
FIG. 13 is a section view taken along lines 13-13 of FIG. 10.

FIG. 1A illustrates the sleeve portion 20 having a generally tubular shape with the unattached side having a diameter that is generally the same as the end portion which attaches to the cap 16. The tubular shape of the sleeve portion extends outwardly in a distal direction, resting above the cap 16. As illustrated in FIG. 1B, the sleeve portion 20 may alternatively be constructed such that the unattached portion has a larger diameter as compared to the attached end. In this manner, the body of the sleeve portion 20 tapers as the sleeve body gets closer to the cap 16. The balloons 13 and 14, see FIG. 3, are expandable by admitting a preferably sterile fluid through one or more control lumen(s) 30 extending through the catheter tube 24. The control lumen(s) 30 extend along the catheter tube 24 substantially parallel to the drain lumen 26. Each control lumen 30 is preferably provided with at least one aperture 32 extending through the side wall of the catheter tube 24. The aperture 32 is preferably positioned in the area of one or more of the balloons 13 and 14 to allow the fluid to enter one or both balloons from the lumen. Check valves, or the like, (not shown), may be utilized to control the flow of fluid into and/or out of the balloons. It should be noted that while the embodiment illustrated only shows one control lumen, multiple control lumens could be provided without departing from the scope of the invention. The tip 10 and sleeve 20 are both preferably made of a biocompatible elastomeric material such as, but not limited to, natural rubber latex, synthetic rubber, plastic, silicone, and platinum cured silicone, and may be prepared, as is known in the art, to include additives, suspensions and/or coatings specially utilized in the process of fabricating catheters and/or catheter balloons or used to prevent sticking together in storage or enhance lubricity. In addition, the inner 40 and/or outer surfaces 42 of the sleeve 20 may include thick sections 44, thin sections 46, ribs 34 or portions to cause the balloons 13 and 14 to inflate to a desired shape. Obviously, the thinner portions of the balloon will afford less resistance to the pressure of the flowing water and hence, will expand more easily than the thicker portion. In a most preferred embodiment, the first balloon 13 is constructed and arranged to expand in a linear as well as a radial relationship to extend past the distal end 12 of the tip 10. The tip 10 and sleeve 20 may be fabricated to be integral or separate by any suitable process which may include but should not be limited to injection molding, dipping, vacuum forming, roto-molding, blow molding or suitable combination(s) thereof. In a most preferred embodiment, the sleeve 20 is formed in an inside-out arrangement. After forming, the sleeve portion 20 is preferably rolled, much like that of a condom. The tip 10 is assembled to the catheter tube 24 by inserting the stem portion 18 of the tip into the drain lumen 26 of the catheter tube until the lower surface 36 of the cap 16 contacts the distal end 22 of the catheter tube 24. Adhesive, solvents, fillers, radio frequency (RF) welding, laser welding or suitable combinations thereof may be utilized to secure the tip to the tube and/or seal the distal end of the catheter tube. Alternatively, the stem portion 18 may contain a securing member (not illustrated) such as barbs, spikes, or the like, to secure the stem portion to the catheter tube. In a preferred embodiment, the distal end 22 and/or the lower surface 36 is covered with an adhesive material thereby forming a circumferential seal. The sleeve portion 20 may then be rolled over the outer surface 28 of the catheter tube 24. At least two spaced apart and circumferentially extending bands of adhesive 38 are positioned about the end portion of the catheter tube to secure the sleeve 20 to the outer surface of the tube while forming the two balloons 13 and 14. Varying the width of the adhesive bands 38 or distance between the adhesive bands allows the size of the balloons to be varied. At least one drain port 50 is preferably positioned between the two balloons, i.e. proximal to balloon 13 and distal to balloon 14, to reduce or prevent the bladder lining from being drawn into the catheter during use. One or more drain ports 250, see FIG. 10, 12, or 14, may optionally be positioned below balloon 214. It should be noted that solvents, radio frequency (RF) welding, laser welding or suitable combinations thereof may be utilized to secure the sleeve to the outer surface of the tube forming the two balloons without departing from the scope of the invention. It should also be noted that the sleeve portion may be dipped into a solution that serves to expand the sleeve material before or after attachment to the catheter tube, such as an alcohol-based fluid, benzene, ether or the like. This expansion may allow for the sleeve portion 20 to be easily rolled over the outer surface of catheter tube, or alternatively, slid over the catheter tube, if left un-rolled. It should further be noted that the portion of the sleeve between the bands of adhesive may be removed or the second balloon may be formed from a second sleeve of material without departing from the scope of the invention.

Figure 7:
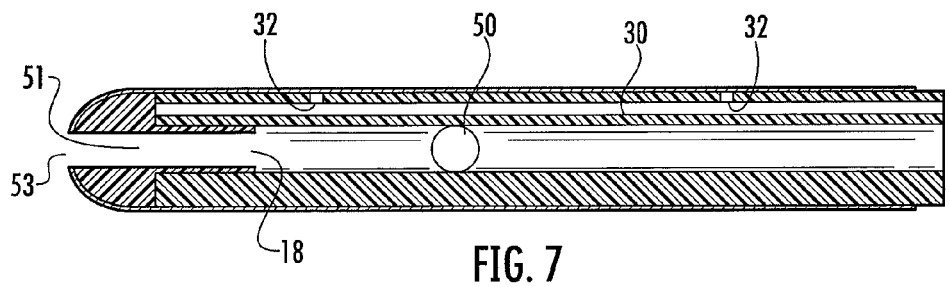
FIG. 7 is a section view taken of one embodiment of the instant invention similar to that of FIG. 4, illustrating an opening at the distal most portion of the tip of the catheter system.
Figure 8:
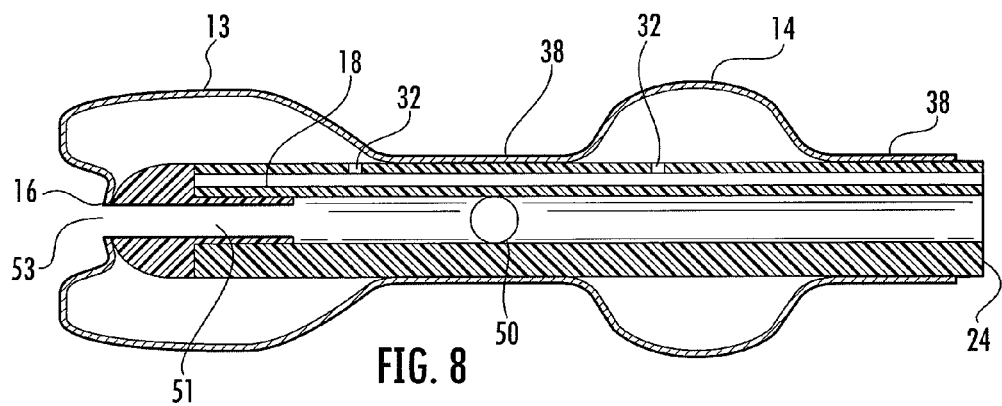
FIG. 8 is a section view taken of one embodiment of the instant invention similar to that of FIG. 6, illustrating an opening at the distal most portion of the tip of the catheter system.
Figure 9:
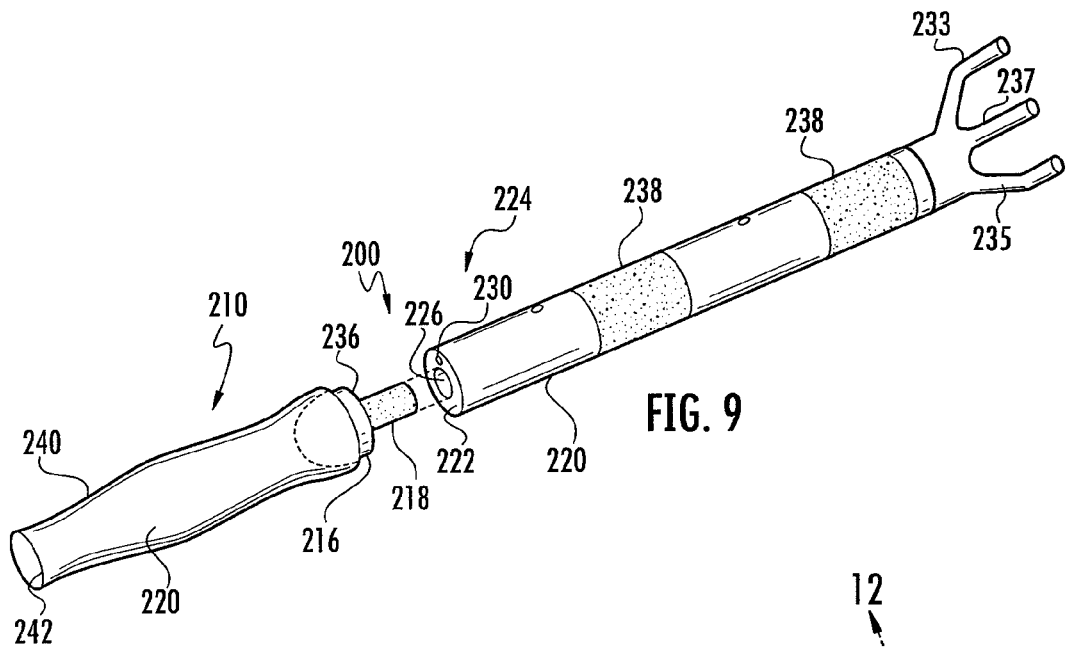
FIG. 9 is an exploded view of an alternative embodiment of the catheter system in accordance with the instant invention, illustrating the tip and sleeve as well as a portion of the catheter tube.

While each of the FIGS. 1-6 illustrate the cap having a closed end, the catheter system or catheter tip may include an internal cavity 51 within the cap 16 and stem portion 18. The internal cavity 51 terminates in an opening 53 and provides fluid flow between the external environment and the distal end 12 of the catheter system 100 or catheter tip 10 to its proximal end 14, see FIGS. 7 and 8.

FIGS. 9-14 illustrates an alternative embodiment of the catheter assembly or catheter tip in accordance with the instant invention. The catheter assembly 200 or catheter tip 210 includes a first balloon 213 constructed and arranged to encapsulate the distal end 212 of the catheter to prevent injury to a body duct, cavity, or vessel, and a second balloon 214 to position the catheter within the body duct, cavity, or vessel (not shown). The catheter tip 210 includes a cap 216 preferably having a stem portion 218 and a sleeve portion 220 secured to or integrally formed with the cap 216. The tip 210 and sleeve 220 are preferably constructed of resiliently flexible biocompatible material(s). The cap portion 216 of the tip 210 is constructed and arranged to be attached to the distal end 212 of a catheter tube 224 while the optional stem 218 is inserted into the drain lumen 226 of the catheter tube 224.

The attached sleeve portion 220 is extended over the outer surface 228 of the end portion of the catheter tube 224 and is selectively attached to the outer surface 228 of the catheter tube 224 in a manner that forms a first balloon 213 positioned to encircle and extend beyond the cap 216 at the distal end of the tube, and at least one second balloon 214 positioned along the catheter tube 224 to retain and/or position the catheter 200 within a body cavity, duct or vessel. The sleeve portion 220 may have a generally tubular shape with the unattached side having a diameter that is generally the same as the end portion which attaches to the cap 216. The tubular shape of the sleeve portion 220 extends outwardly in a distal direction, resting above the cap 216.

Alternatively, the sleeve portion 220 may be constructed such that the unattached portion has a larger diameter as compared to the attached end. In this manner, the body of the sleeve portion 220 therefore tapers as the sleeve body gets closer the cap 216, similar to that illustrated in FIG. 1B. The balloons 213 and 214 are expandable by admitting a preferably sterile fluid through a plurality of control lumens 230A and 230B extending through the catheter tube 24. The control lumens 230A/230B extend along the catheter tube 224 substantially parallel to the drain lumen 226. The control lumens 230A and 230B are preferably provided with at least one aperture 232 extending through the side wall of the catheter tube 224. The aperture 232 is preferably positioned in the area of one or more of the balloons 213 and 214 to allow the fluid to enter one or both balloons from the lumen.

Check valves 233, 235, or the like, may be utilized to control the flow of fluid into and/or out of the balloons. It should be noted that while the embodiment illustrated shows control lumen 230A and 230B as lumens for the purpose of inflation of the balloons, control lumens 230A or 230B can be used to dispense, aspirate, or combinations thereof, fluid into or out of the body duct, cavity, or vessel without departing from the scope of the invention. To accomplish such a task, the catheter tube 224 may contain an additional aperture which provides fluid communication with the control lumen 230A and 230B and the external environment, i.e. the body cavity. Additionally, valve 237 is utilized to control the flow of fluid into and/or out of the main drainage lumen 226. The tip 210 and sleeve 220 are both preferably made of a biocompatible elastomeric material such as, but not limited to, natural rubber latex, synthetic rubber, plastic and silicone and may be prepared, as is known in the art, to include additives, suspensions and/or coatings specially utilized in the process of fabricating catheters and/or catheter balloons or used to prevent sticking together in storage or enhance lubricity.

In addition, the inner 240 and/or outer surfaces 242 of the sleeve 220 may include thick sections and/or thin sections, ribs, similar to that illustrated and described previously, or portions to cause the balloons 213 and 214 to inflate to a desired shape. Obviously, the thinner portions of the balloon will afford less resistance to the pressure of the flowing water and hence, will expand more easily than the thicker portion. In a most preferred embodiment, the first balloon 213 is constructed and arranged to expand in a linear as well as a radial relationship to extend past the distal end 212 of the tip 210. The tip 210 and sleeve 220 may be fabricated to be integral or separate by any suitable process which may include but should not be limited to injection molding, dipping, vacuum forming, roto-molding, blow molding or suitable combination(s) thereof. In a most preferred embodiment, the sleeve 220 is formed in an inside-out arrangement.

After forming, the sleeve portion 220 is preferably rolled, much like that of a condom. The tip 210 is assembled to the catheter tube 224 by inserting the stem portion 218 of the tip into the drain lumen 226 of the catheter tube until the lower surface 236 of the cap 216 contacts the distal end 222 of the catheter tube 224. Adhesive, solvents, fillers, radio frequency (RF) welding, laser welding or suitable combinations thereof may be utilized to secure the tip to the tube and/or seal the distal end of the catheter tube. Alternatively, the stem portion 218 may contain a securing member (not illustrated) such as barbs, spikes, or the like, to secure the stem portion to the catheter tube. The sleeve portion 220 may then be rolled over the outer surface 228 of the catheter tube 224.

At least two spaced apart and circumferentially extending bands of adhesive 238 are positioned about the end portion of the catheter tube to secure the sleeve 220 to the outer surface of the tube while forming the two balloons 213 and 214. Varying the width of the adhesive bands 238 or distance between the adhesive bands allows the size of the balloons to be varied. At least one drain port 250 is preferably positioned between the two balloons, i.e. proximal to balloon 13 and distal to balloon 14, to reduce or prevent the bladder lining from being drawn into the catheter during use. One or more drain ports 250 may optionally be positioned below balloon 214. It should be noted that solvents, radio frequency (RF) welding, laser welding or suitable combinations thereof may be utilized to secure the sleeve to the outer surface of the tube forming the two balloons without departing from the scope of the invention. It should also be noted that the sleeve portion may be dipped into a solution that serves to expand the sleeve material before or after attachment to the catheter tube, such as an alcohol-based fluid, benzene, ether or the like. This expansion may allow for the sleeve portion 220 to be easily rolled over the outer surface of catheter tube, or alternatively, slid over the catheter tube, if left un-rolled. It should further be noted that the portion of the sleeve between the bands of adhesive may be removed or the second balloon may be formed from a second sleeve of material without departing from the scope of the invention.

Figure 14:
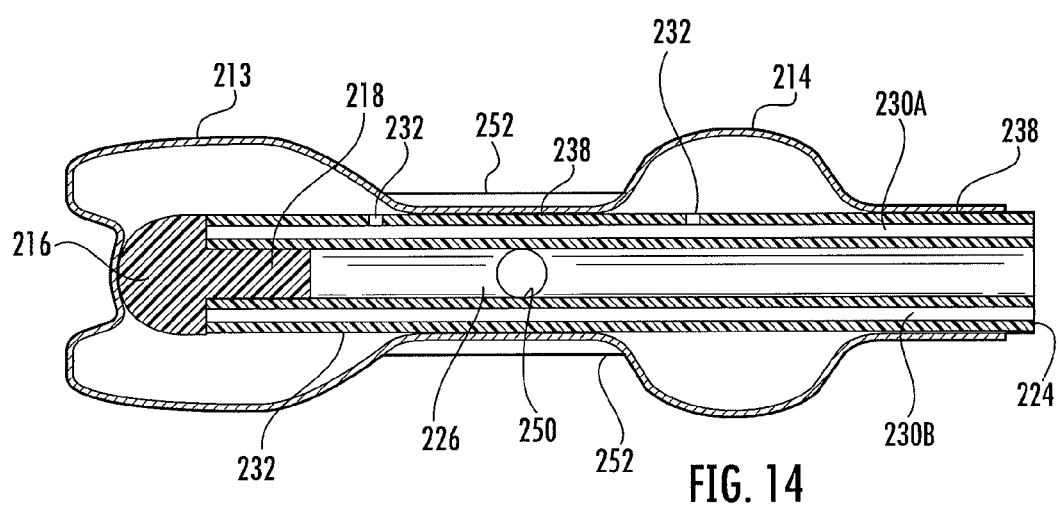
FIG. 14 is a section view taken along lines 14-14 of FIG. 11 illustrating the balloons in an expanded condition.
Figure 15:
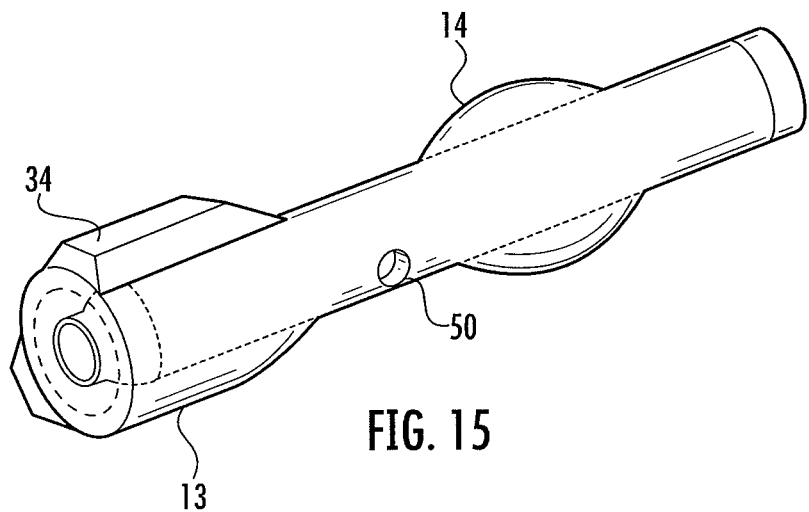
FIG. 15 is a perspective view of one embodiment of the instant invention illustrating one rib longitudinally aligned on the distal most expanded balloon.
Figure 16:
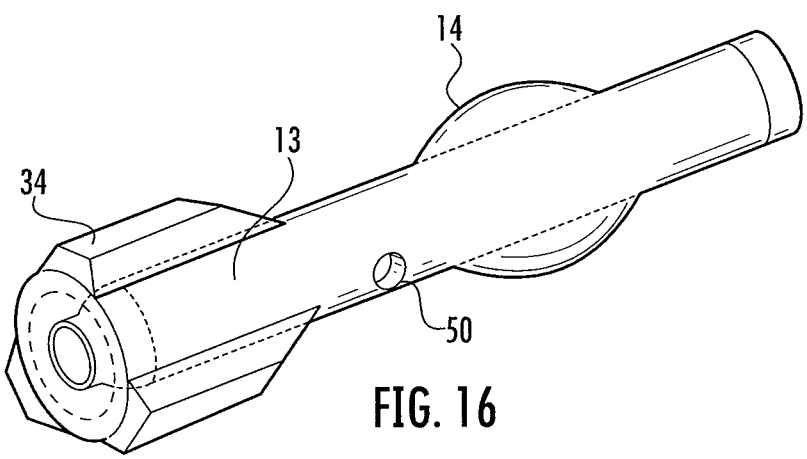
FIG. 16 is a perspective view of one embodiment of the instant invention illustrating a plurality of ribs longitudinally aligned on the distal most expanded balloon.
Figure 17:
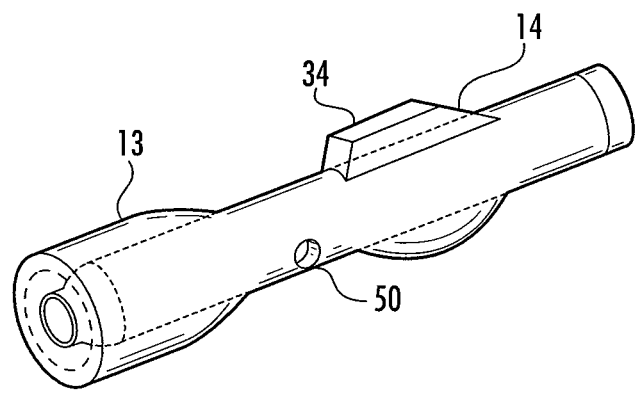
FIG. 17 is a perspective view of one embodiment of the instant invention illustrating one rib longitudinally aligned on the proximal most expanded balloon.
Figure 18:
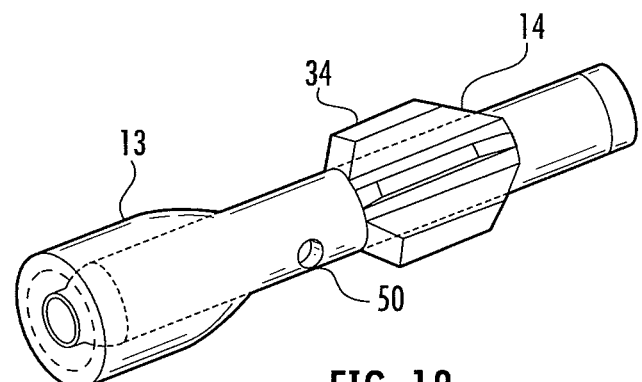
FIG. 18 is a perspective view of one embodiment of the instant invention illustrating a plurality of ribs longitudinally aligned on the proximal most expanded balloon.

Optionally, the catheter system 200 may contain a support member which is positioned between balloons 213 and 214, see FIG. 14. The support member 252, which may be, for example, a sleeve member or support walls, minimizes the effects of lateral motion on balloons 213 and 214 and prevents balloon 213 from tipping over onto balloon 214.

Each of the balloons 13 (213) and 14 (214) may be designed to inflate to any size necessary. In a preferred embodiment, the balloon size of one balloon, for example balloon 13 is designed to be smaller when inflated than the balloon size of the other balloon, i.e. balloon 14. The difference between sizes of the two balloons can vary depending in the use of the catheter. In an illustrative example, the difference between balloon 13 and balloon 14 could be in the range of approximately 20% to 80%, based on the actual size of the fully inflated balloons or based on the injection volume of each of the balloons. The sizing of balloon 13, for example, can be designed such that a maximum size of the balloon is not too large so as to be susceptible to bending. Since the preferred embodiment described a double balloon with drainage aperture for providing drainage of fluid from a bladder, should the balloon 13 be too large and bend, the catheter may become inefficient as a result of the formation of a kink. Formation of such a kink results in sealing of the drainage aperture and blocks the balloon's inflation lumen. In addition to preventing fluid flow, the ability of the balloon 13 to deflate will be limited or completely prevented. Each of the balloons 13 and 14 may additionally be made of materials having deferent thickness and/or durometer values. Such differing thickness may result in inflation of the balloons at differing rates. In a preferred embodiment, the thickness of each of the balloons can be designed such that balloon 14 inflates before the balloon 13. Inflation in this manner provides enhanced safety measures. For example, in use as a urinary catheter, ensuring that the proximal balloon (balloon 14) inflates before the distal balloon (balloon 13) ensures that no balloon will be inflated within the urethra.

FIGS. 15-22 illustrate various embodiments of balloons 13 and 14 of the catheter system 100 or catheter tip 10 constructed with a plurality of areas of varying thicknesses to create ribs, lobes and variously shaped balloons. While such figures are illustrative of the catheter system 100 and catheter tip 10, each of the embodiments described are applicable to the catheter system 200 and catheter tip 210 or any system/tip in accordance with the instant invention. The balloon 13, the balloon 14, or both balloon 13 and 14 may contain ribs 34 or lobes 52. While each of the balloons may contain any number of ribs 34 or lobes 52, a preferred embodiment provides for at least 3 ribs 34 or lobes 52 longitudinally along the balloon 13. The rib 34 or lobe 52 begins at the most distal end and terminates at approximately the half-way point the balloon. The formation of the ribs or lobes functions to add strength to the balloon, allow residual fluid, i.e. urine, to run off the tip of the balloon, and when inflated provide an area of recess.

In addition to, or instead of, balloon 14 may also contain ribs 34 or lobes 52. While such ribs and lobes may be aligned radially, a preferred embodiment includes the ribs and lobes being aligned longitudinally, and extending from the distal end. Use of ribs and lobes along balloon 14 allows the entire balloon or portions of it, to inflate more than standard balloons, thus bringing balloon 13 and 14 closer together when both are fully or partially inflated, thereby minimizing tissue aspiration into the drainage apertures and preventing the balloon 13 from bending over, or top over and forming kinks. FIG. 19 shows an illustrative example of the catheter system 100 having a plurality of lobes 52 formed at the top end of balloon 14. Should balloon 13 became misaligned, see FIG. 20, the lobes 52 prevent the balloon from complete top over and allow for the balloon 13 to return to its original position. FIG. 21 illustrates use of a plurality of lobes formed on both of the balloons 13 and 14. As illustrated, the lobes 52 can be positioned along the distal end (top edge) 52A, the proximal end (bottom edge) 52B, or combinations thereof, see balloon 14. The lobes formed on both balloons 13 and 14 may be aligned in substantially the same plan when each of the balloons are inflated and are in the proper alignment, see FIG. 21. Should the balloon 13 become misaligned and tip, see FIG. 22, the lobes associated with balloon 14 contact the lobes of balloon 13, thereby limiting the degree of top over, preventing kinking, and blocking of the drainage aperture.

Figure 23:
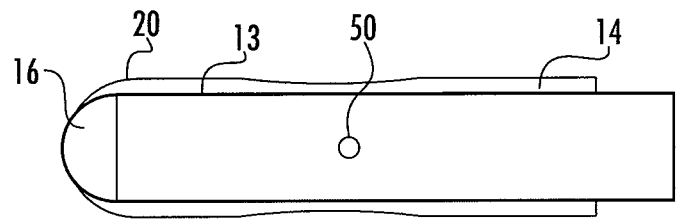
FIG. 23 is a perspective view of the catheter tip in accordance with the instant invention, illustrated in the non-inflated state.
Figure 24:
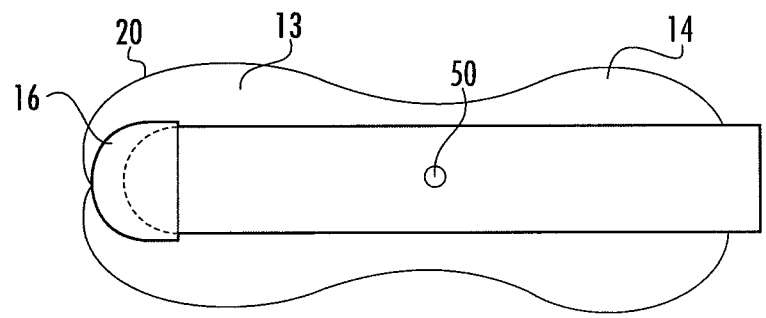
FIG. 24 is a perspective view of the catheter tip in accordance with the instant invention, illustrated in the partially inflated state.
Figure 25:
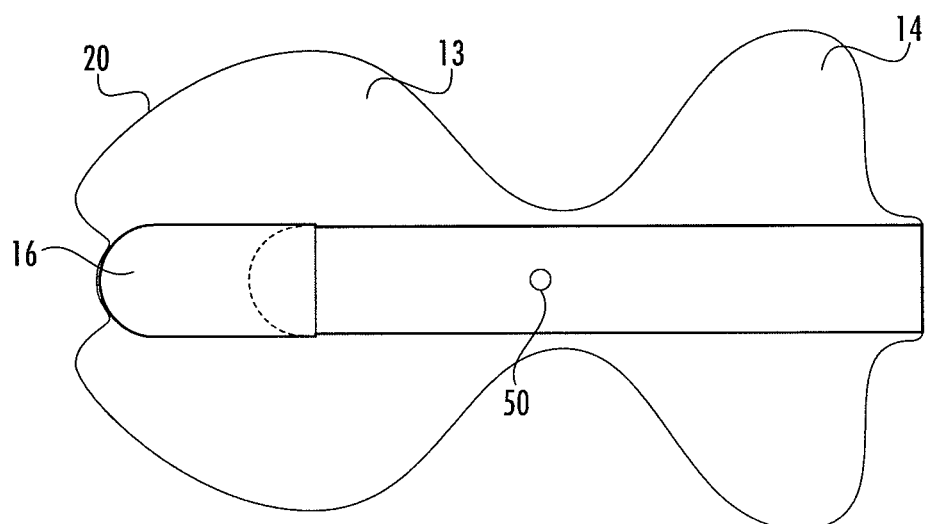
FIG. 25 is a perspective view of the catheter tip in accordance with the instant invention, illustrated in the fully inflated state.

In a preferred embodiment, the cap 16 is constructed and arranged to provide traversal between a resting stage and an elongated state; preferably through the type of material it is constructed of and through control of its thickness and/or resistance to change shapes. FIG. 23 illustrates the cap 16 in its resting state. In this configuration, the balloons have not been inflated. As the balloons receive an inflation fluid and inflate, see FIG. 24, the shape of the cap 16 traverses from its resting state to an inflation state. In this second configuration, the cap 16 elongates, see FIG. 25, as the balloons take in fluid and fully inflate. The degree of elongation can vary depending on the material used, the durometer of the balloons and/or cap, or the length pulled. In a preferred embodiment, the cap 16 is constructed to elongate a distance in the range of approximately 10%-200% relative the length of the cap at its resting state. As the inflation fluid is removed and the balloons deflate, cap 16 retains its original starting shape.

Although this invention has been shown and described with respect to detailed embodiments thereof, it will be appreciated and understood by those skilled in the art that various changes in form and detail thereof may be made without departing from the spirit and scope of the disclosed invention.

What is claimed is:

1. A catheter assembly having an encapsulatable catheter tip for encapsulating a distal end of the catheter thereby minimizing the risk of infection comprising:
a catheter body having a distal end, a proximal end, and at least one main lumen extending generally from said distal end to said proximal end to provide fluid flow therebetween, and at least one control lumen positioned in a parallel arrangement with said main lumen and adapted for providing fluid communication with one or more balloons;
a catheter tip cap having a solid distal end and a proximate end constructed and arranged to secure to a top surface of said catheter body and a cylindrical stem portion having an outer surface which engages with an inner surface of said at least one said main lumen, said catheter tip cap having an integrally formed sleeve which forms a first balloon constructed and arranged to provide a barrier between said tip and a body duct, tissue cavity or vessel and a second balloon constructed and arranged to position said catheter within said body duct, cavity, or vessel;
at least said solid portion of said tip cap adapted to elongate along a longitudinal axis of said catheter body as said first balloon traverses between a first non-inflated position and a second inflated position and return to its original shape when said first balloon returns to said first non-inflated state;
whereby engagement of said cylindrical stem portion with said catheter body maintains said first or second balloon in a centered position when inflated;
whereby inflation of said first balloon results in encapsulation of said distal end of said catheter, thereby preventing damage to said body duct, tissue cavity or vessel and inflation of said second balloon provides securing of said catheter to said body duct, tissue cavity, or vessel.

2. The catheter assembly according to claim 1 wherein said catheter body includes three or more lumens.

3. The catheter assembly according to claim 1 wherein at least one lumen is fluidly connected to said first balloon, said second balloon, or combinations thereof.

4. The catheter assembly according to claim 1 wherein said first and said second balloons expand in a linear fashion, radial fashion, or combinations thereof.

5. The catheter assembly according to claim 1 wherein said catheter body includes at least one drainage aperture for drainage of a fluid, said aperture being located proximal to said first balloon and distal to said second balloon.

6. A catheter assembly having an encapsulatable catheter tip for encapsulating a distal end of the catheter thereby minimizing the risk of infection comprising:
a catheter body having a distal end, a proximal end, and a plurality of lumens extending generally from said distal end to said proximal end, said plurality of lumens including at least one drainage lumen in fluid communication with a drainage port for providing fluid flow within said drainage lumen, and at least one control lumen, said control lumen being in fluid communication with a sleeve member for providing inflation of said sleeve thereby forming at least a first and second balloon;
a catheter tip cap comprising a closed distal end and a proximal end constructed and arranged to be secured to a top surface of said distal end of said catheter body and a generally solid cylindrical stem portion projecting outwardly from said proximal end and securing to an inner surface of at least one of said plurality of lumens, said catheter tip cap having said sleeve member which contains a first end integrally formed at or near said distal end of said catheter tip cap and a second end secured to a plurality of positions along said catheter body, thereby forming a first balloon constructed and arranged to provide a barrier between said catheter tip and a body duct, tissue cavity or vessel, and a second balloon constructed and arranged to position said catheter within said body duct, tissue cavity or vessel;
said tip cap distal end, proximal end, solid cylindrical stem portion, or combinations thereof, adapted to elongate along a longitudinal axis of said catheter body as said one or more balloons traverses between a first non-inflated position and a second inflated position and return to its original shape when said one or more balloons return to said first non-inflated state;
whereby inflation of said first balloon results in encapsulation of said distal end of said catheter thereby preventing damage to said body duct, tissue cavity or vessel, and inflation of said second balloon provides securing of said catheter to said body duct, tissue cavity, or vessel.

7. The catheter assembly according to claim 6 wherein said plurality of lumens includes at least one lumen which is fluidly connected to the external environment for dispensing fluids from said lumen to the external environment, aspirating fluids from the external environment to said lumen, or combinations thereof.

8. The catheter assembly according to claim 6 wherein said stem portion contains one or more securing members.

9. The catheter assembly according to claim 8 wherein said securing members are barbs.

10. The catheter assembly according to claim 6 wherein said cap is secured to said catheter body through adhesives, solvents, fillers, radio frequency (RF) welding, laser welding, or combinations thereof.

11. The catheter assembly according to claim 6 wherein at least one drain port is positioned proximally to said first balloon and distally to said second balloon, said positioning minimizing or preventing the lining of said body duct, tissue cavity, or vessel from being drawn into the catheter during use.

12. The catheter assembly according to claim 6 wherein the size of each said balloon is varied.

13. The catheter assembly according to claim 12 wherein said first balloon is larger than said second balloon.

14. The catheter assembly according to claim 12 wherein said first balloon is smaller than said second balloon.

15. The catheter assembly according to claim 6 wherein the outer surface of said sleeve includes one or more thick sections, one or more thin sections, or combinations thereof, for providing varied regions along said balloons which have varied resistance to inflation.

16. The catheter assembly according to claim 15 wherein said first balloon, said second balloon, or combinations thereof contain one or more lobes.

17. The catheter assembly according to claim 16 wherein each of said balloons contain one or more lobes, said one or more lobes of said first balloon and said one or more lobes of said second balloon are aligned in such a manner so as should said first balloon and said second balloon become misaligned, a proper spacing between said misaligned balloons is maintained such that said first balloon does not completely block fluid flow from the external environment to within said drainage lumen, thereby preventing said drainage port from being obstructed.

18. The catheter assembly according to claim 6 wherein said first balloon, said second balloon, or combinations thereof contain one or more ribs.

19. The catheter assembly according to claim 18 wherein said ribs are arranged circumferentially along said balloons.

20. The catheter assembly according to claim 19 wherein the outer surface, the inner surface, or combinations thereof, of said first balloon has a greater resistance to inflation than the outer surface, the inner surface, or combinations thereof, of said second balloon, whereby said second balloon inflates prior to the inflation of said first balloon.

21. The catheter assembly according to claim 18 wherein said ribs are arranged longitudinally along said balloons.

22. A catheter tip cap for securing to a catheter and forming an end portion thereof, comprising: a catheter tip cap having a main body having a closed distal end having a surface sized and shaped to secure to an end portion of a catheter tube and a proximal end having a generally solid cylindrical stem portion sized and shaped to secure within an interior lumen of an end portion of a catheter tube thereby forming a seal on said end portion of said catheter tube; and a sleeve, said sleeve integrally formed to the distal end of said main body portion, wherein said sleeve is constructed and arranged to form a first balloon and a second balloon when said main body is in cooperative engagement with said catheter tube, said main body adapted to elongate as said at least one balloon traverses between a first non-inflated position and a second inflated position and return to its original shape when said at least one balloon returns to said first non-inflated state.

23. The catheter tip cap for securing to a catheter system and forming an end portion thereof, according to claim 22 wherein said sleeve is constructed and arranged to form at least two inflation members in the form of a first balloon and a second balloon when said main body is in cooperative engagement with said catheter tube, whereby at least one balloon is constructed and arranged to prevent the distal end of the catheter from impinging against the inner wall of a body duct, cavity or vessel and at least one balloon is constructed and arranged to position the catheter within said body duct, cavity or vessel.

24. The catheter tip cap for securing to a catheter system and forming an end portion thereof, according to claim 23 wherein at least one balloon extends radially and axially beyond said distal end of the catheter.

25. The catheter tip cap for securing to a catheter system and forming an end portion thereof, according to claim 24 wherein said sleeve contains ribs.

26. The catheter tip cap for securing to a catheter system and forming an end portion thereof, according to claim 22 wherein said sleeve contains a combination of areas having different thicknesses to provide a shape or direct the expansion of the balloon in a desired direction or area.

27. The catheter tip cap for securing to a catheter system and forming an end portion thereof, according to claim 22 wherein said sleeve contains a drain port, said drain port being in fluid communication with a drainage lumen of said catheter tube for providing fluid flow from said body duct, cavity or vessel to said drainage lumen.

28. The catheter tip cap for securing to a catheter system and forming an end portion thereof according to claim 22 wherein said sleeve contains a combination of areas of differing thicknesses to provide expansion of said first balloon at a different rate than said second balloon.

29. The catheter tip cap for securing to a catheter system and forming an end portion thereof, according to claim 22 wherein said main body is made of a biocompatible elastomeric material.

30. The catheter tip cap for securing to a catheter system and forming an end portion thereof, according to claim 22 wherein said main body is made of a biocompatible elastomeric material which when in cooperative engagement with said catheter tube can elongate along a longitudinal axis of said main body as at least one balloon traverses between a first non-inflated position and a second inflated position.

31. The catheter tip cap for securing to a catheter system and forming an end portion thereof according to claim 22 wherein said sleeve is made of a biocompatible elastomeric material.

32. A urinary catheter assembly having an encapsulated catheter tip for encapsulating a distal end of the urinary catheter thereby minimizing the risk of infection comprising:
a urinary catheter body having a distal end, a proximal end, and a plurality of lumens extending generally from said distal end to said proximal end, said plurality of lumens including at least one drainage lumen in fluid communication with a drainage port for providing urine flow within said drainage lumen, and at least one control lumen, said control lumen being in fluid communication with a sleeve member for providing inflation of said sleeve thereby forming a first balloon and a second balloon;
a urinary catheter tip cap comprising a closed distal end and a proximal end having at least one surface for securing to a surface of said urinary catheter body and a generally solid cylindrical stem projecting outwardly from said proximal end, said cylindrical solid stem of said tip cap constructed and arranged to cooperate with one of said plurality of lumens, at least a portion of said tip cap independent of said balloons adapted to elongate along a longitudinal axis of said main body as at least one balloon traverses between a first non-inflated position and a second inflated position and returns to its original shape when said at least one balloon returns to said first non-inflated state; said urinary catheter tip cap having said sleeve member which contains a first end integrally formed to said distal of said catheter tip cap and a second end secured to a plurality of positions along said urinary catheter body, thereby forming a first balloon constructed and arranged to provide a barrier between said urinary catheter tip and a bladder, and a second balloon constructed and arranged to position said catheter within said bladder;
whereby inflation of said first balloon results in encapsulation of said distal end of said urinary catheter thereby preventing damage to the mucosal lining of said bladder, and inflation of said second balloon provides securing of said urinary catheter to said bladder.

* * * * *